US008846394B2

(12) United States Patent
Mistry et al.

(10) Patent No.: US 8,846,394 B2
(45) Date of Patent: Sep. 30, 2014

(54) TREATMENT OF NEUROLOGICAL DEFICITS IN THE STRIATUM OR SUBSTANTA NIGRA PARS COMPACTA

(75) Inventors: Sanjay Mistry, Downingtown, PA (US); Darin J. Messina, Downingtown, PA (US)

(73) Assignee: Ethicon, Inc., Somerville, NJ (US)

( * ) Notice: Subject to any disclaimer, the term of this patent is extended or adjusted under 35 U.S.C. 154(b) by 1015 days.

(21) Appl. No.: 12/268,647

(22) Filed: Nov. 11, 2008

(65) Prior Publication Data

US 2009/0149371 A1 Jun. 11, 2009

Related U.S. Application Data

(63) Continuation of application No. 10/952,064, filed on Sep. 28, 2004, now abandoned.

(51) Int. Cl.
*C12N 5/07* (2010.01)
*A61K 38/18* (2006.01)
*A61K 38/17* (2006.01)

(52) U.S. Cl.
CPC ......... *A61K 38/1875* (2013.01); *A61K 38/1825* (2013.01); *A61K 38/1709* (2013.01)
USPC ....................................................... 435/377

(58) Field of Classification Search
None
See application file for complete search history.

(56) References Cited

U.S. PATENT DOCUMENTS

| | | | |
|---|---|---|---|
| 5,093,317 A | 3/1992 | Lewis et al. | |
| 5,670,483 A | 9/1997 | Zhang et al. | |
| 5,750,376 A * | 5/1998 | Weiss et al. | 435/69.52 |
| 5,795,908 A * | 8/1998 | Hamilton et al. | 514/423 |
| 5,955,343 A | 9/1999 | Holmes et al. | |
| 6,506,729 B1 | 1/2003 | Rueger et al. | |
| 6,531,450 B2 * | 3/2003 | Hotten et al. | 514/12 |
| 2002/0160471 A1 | 10/2002 | Kisiday | |
| 2003/0161818 A1 | 8/2003 | Weiss et al. | |
| 2005/0032209 A1 * | 2/2005 | Messina et al. | 435/366 |
| 2005/0037491 A1 | 2/2005 | Mistry | |
| 2005/0054098 A1 * | 3/2005 | Mistry et al. | 435/372 |
| 2005/0058631 A1 * | 3/2005 | Kihm et al. | 424/93.7 |
| 2006/0223177 A1 | 10/2006 | Harris | |
| 2006/0233765 A1 | 10/2006 | Messina | |
| 2006/0234376 A1 * | 10/2006 | Mistry et al. | 435/366 |
| 2007/0009494 A1 | 1/2007 | Mistry | |
| 2007/0014771 A1 | 1/2007 | Mistry | |
| 2007/0036767 A1 | 2/2007 | Mistry | |

FOREIGN PATENT DOCUMENTS

| | | |
|---|---|---|
| WO | WO 93/16099 A2 | 8/1993 |
| WO | WO 95/04819 A1 | 2/1995 |
| WO | WO 97/03188 | 1/1997 |
| WO | WO 99/15191 | 4/1999 |
| WO | WO 02/062969 A2 | 8/2002 |
| WO | WO 02/082074 | 10/2002 |
| WO | WO 03/000868 A1 | 1/2003 |
| WO | 03/080822 A1 | 10/2003 |
| WO | WO 2004/081172 | 9/2004 |

OTHER PUBLICATIONS

Ye 1998 (Cell 93:755-766).*
Sullivan 1999 (Brain Research 818:176-179).*
Balis, F.M. et al., "Central Nervous System Pharmacology of Antileukemic Drugs", The American Journal of Pediatric Hematology/Oncology, 1989, vol. 11(1), pp. 74-86.
Chalazonitis, A. et al., "Transforming Growth Factor Beta Has Neurotrophic Actions on Sensory Neurons in Vitro and Is Synergistic with Nerve Growth Factor", Developmental Biology, 1992, vol. 152, pp. 121-132.
Kingsley, D.M.,"The TGF-Beta Superfamily: New Members, New Receptors, and New Genetic Tests of Function in Different Organisms", Genes & Development, 1994, vol. 8 pp. 133-146.
Krieglstein K. et al., "TGF-Beta Superfamily Members Promote Survival of Midbrain Dopaminergic Neurons and Protect Them Against MPP+ Toxicity", The EMBO Journal, 1995, vol. 14, No. 4, pp. 736-742.
Krieglstein K. et al., "Trophic and Protective Effects of Growth/Differentiation Factor 5, a Member of the Transforming Growth Factor-Beta Superfamily, on Midbrain Dopaminergic Neurons", Journal of Neuroscience Research, 1995, vol. 42, pp. 724-732.
Lundborg, G., "Nerve Regeneration and Repair", Acta Orthopaedica Scandinavica, 1987, vol. 58(2), pp. 145-169.
Martinou, J., "Transforming Growth Factor Beta$_1$ is a Potent Survival Factor for Rat Embryo Motoneurons in Culture", Developmental Brain Research, 1990, vol. 52, pp. 175-181.
Roberts, A.B. and Sporn, M.B., "The Transforming Growth Factor-Betas", Handbook of Experimental Pharmacology, eds. Sporn and Roberts, 1990, vol. 95, pp. 419-472.
Roussa, E. et al., "TGF-beta promotes survival on mesencephalic dopmainergic neurons in cooperatin with Shh and FGF-8", Neurobiology of Disease, 2004, vol. 16, pp. 300-310.
Sakurai, T., "Activin A Stimulates Mitogenesis in Swiss 3T3 Fibroblasts Without Activation of Mitogen-Activated Protein Kinases", The Journal of Biological Chemistry, 1994, vol. 269(19) May 13, pp. 14118-14122.
Sullivan, A.M. et al., "Growth/differentiation factor 5 protects nigrostrialtal dopaminergic neurons in a rat model of Parkinson's disease", Neuroscience Letters, 1997, vol. 233, pp. 73-76.
Jakel R.J. et al., "Using Human Neural Stem Cells to Model Neurological Disease", Nature Reviews Genetics, 2004, vol. 5(2), pp. 136-144.
Gerard W. O'Keeffe et al., "Effects of growth/differentiation factor 5 on the survival and morphology of embryonic rat midbrain dopaminergic neurons in vitro", Journal of Neurocytology, Klumer Academic Publishers, BO, vol. 33, No. 5, Sep. 1, 2004, pp. 479-488.

(Continued)

*Primary Examiner* — Gregory S Emch

(57) ABSTRACT

The present invention is directed to methods of treating neurological deficits resulting from injury or disease to the striatum or substanta nigra pars compacta of a human by administering human recombinant GDF5 to the striatum or substanta nigra pars compacta of a human in amounts effective to induce cell populations having the capacity to differentiate towards a dopaminergic phenotype to in fact differentiate towards a dopaminergic phenotype, and to neurotrophic compositions and matrices suitable for use in such treatments.

3 Claims, No Drawings

(56) References Cited

OTHER PUBLICATIONS

Hurley F.M., et al., "Neuroprotective effects of delayed administration of growth/differentiation factor-5 in the partial lesion model of Parkinson's disease", Experimental Neurology, Academic Press, vol. 185, No. 2, Feb. 1, 2004, pp. 281-289.

Ye, Weilan et al., "FGF and Shh signals control dopamingergic and serotenergic cell fate in the anterior neural plate", Cell, vol. 93, No. 5, May 29, 1998, pp. 755-766.

MP52-Related Nomenclature, Bio Pharm Oct. 28, 2004, pp. 1-4.

\* cited by examiner

TREATMENT OF NEUROLOGICAL DEFICITS IN THE STRIATUM OR SUBSTANTA NIGRA PARS COMPACTA

This application is a continuation of application Ser. No. 10/952,064, filed Sep. 28, 2004 now abandoned.

FIELD OF INVENTION

The present invention is directed to methods of treating neurological deficits resulting from injury or disease to the striatum or substanta nigra pars compacta of a human by administering human recombinant GDF5 thereto, and to compositions and matrices containing human recombinant GDF5 for use in such methods of treatment.

BACKGROUND OF THE INVENTION

No satisfactory method exists to repair the damage caused by neuropathies, such as may be attributable to Parkinson's disease (Parkinsonism) or stroke. Parkinson's disease is a syndrome consisting of neurological deficits such as tremor, rigidity, brady- and hypokinesia, and other deficits in equilibrium and posture. Parkinson's disease is often associated with the aging of the nervous system. Similarly, stroke can affect the motor system, rendering the patient with symptoms of hemiparesis or paralysis.

The substantia nigra is the principal site of pathology in Parkinson's disease. Pigmented neurons of the substantia nigra project widely and diffusely to the caudate-putamen (corpus striatum) and are specialized to synthesize and release dopamine. Symptoms of Parkinsonism emerge when 75-80% of the dopaminergic innervation is destroyed. Patients with Parkinson's disease respond to dopamine replacement therapy. Unfortunately, the efficacy of dopamine replacement therapy decreases progressively with continued degeneration of the nigrostriatal dopaminergic pathway.

The identification of stem cells has stimulated research aimed at the selective generation of specific cell types for regenerative medicine. Although protocols have been developed for the directed differentiation of stem cells into therapeutically relevant cell types, such as dopaminergic (DA) neurons for the treatment of Parkinson's, motor neurons for the treatment of ALS, and oligodendrocytes for the treatment of MS, the efficient generation of substantial numbers of these cell types from stem cells has not yet been reported. The ability to generate unlimited numbers of DA neurons that express the full complement of midbrain DA neuron markers is an important part to providing a cure for Parkinson's. Thus, agents that can be utilized to stimulate the differentiation of stem cells to the DA lineage provide a potential to harness and differentiate both exogenous and endogenous stem cells for Parkinson's as well as stokes affecting the middle cerebral artery (MCA) and its branches.

In other cases, attempts to counteract the effects of acute or neurodegenerative lesions of the brain and/or spinal cord have primarily involved implantation of embryonic neurons in an effort to compensate for lost or deficient neural function. However, human fetal cell transplantation research is severely restricted. Administration of neurotrophic factors such as nerve growth factor and insulin-like growth factor also have been suggested to stimulate neuronal growth within the central nervous system (CNS). See, e.g., Lundborg, Acta Orthop. Scand. 58: 145-169 (1987); U.S. Pat. No. 5,093,317. Administration of neurotrophic factors to the CNS requires bypassing the blood-brain barrier. The barrier may be overcome by direct infusion, or by modifying the molecule to enhance its transport across the barrier, as by chemical modification or conjugation, or by molecule truncation. Many growth factors from the TGF-beta superfamily [Kingsley, Genes & Development 8 133-146 (1994)] and the literature cited therein are relevant for a wide range of medical treatment methods and applications which in particular concern wound healing and tissue regeneration. Some of these multifunctional proteins also have survival promoting effects on neurones in addition to functions such as regulation of the proliferation and differentiation in many cell types [Roberts and Sporn, Handbook of Experimental Pharmacology 95 419-472, eds. Sporn and Roberts (1990); Sakurai et al., J. Biol. Chem., 269 14118-14122 (1994)]. Thus for example trophic effects on embryonic motor and sensory neurones were demonstrated for TGF-beta in vitro [Martinou et al., Devl. Brain Res., 52 175-181 (1990); Chalazonitis et al., Dev. Biol., 152 121-132 (1992)]. In addition effects promoting survival were shown on dopaminergic neurones of the midbrain for the proteins TGF-beta-1, -2, -3, activin A and GDNF (glial cell line-derived neurotrophic factor), a protein which has structural similarities to TGF-beta superfamily members but these effects were not mediated via astrocytes [Krieglstein et al., EMBO J., 14, 736-742 (1995)]. The occurrence of proteins of the TGF-beta superfamily in various tissue and developmental stages corresponds with differences with regard to their exact functions as well as target sites, life-span, requirements for auxiliary factors, necessary cellular physiological environment and/or resistance to degradation.

GDF5 is expressed in the neonatal rat midbrain, suggesting that it may play a role in the development of dopaminergic neurons [Krieglstein et al., J. Neurosci. Res., 42 724-32 (1995)]. In vitro studies have demonstrated that MP52 has survival-promoting actions on embryonic rat dopaminergic neurons protecting them against the toxin 1-methyl-4-pyridinium (MPP+). Moreover, in vivo studies have demonstrated that intraparenchymal injection of GDF5 protects the adult rat nigrostriatal dopaminergic system from death induced by 6-hydroxydopamine (6OHDA) lesion of the medial forebrain bundle [Sullivan et al., Eur. J. Neurosci., 233 73-6 (1997)]. However, while such studies indicate that GDF5 appears to play important roles in the development and protection of the dopaminergic limbic system, they do not address or shed any light on the relevance of GDF5 with respect to neuroregenerative capacity or the ability to differentiate endogenous or exogenous cell populations.

Accordingly, there is a need for treatment of neurological deficits resulting from injury or disease to the striatum or substanta nigra pars compacta of a human.

The present invention seeks to utilize human recombinant GDF5 in a manner that enables the treatment or prevention of such resulting deficits.

SUMMARY OF THE INVENTION

The present invention is directed to methods of treating neurological deficits resulting from injury or disease to the striatum or substanta nigra pars compacta of a human comprising administering human recombinant GDF5 to the striatum or substanta nigra pars compacta of a human in amounts effective to induce cell populations having the capacity to differentiate towards a dopaminergic phenotype to in fact differentiate cells towards said dopaminergic phenotype, and to compositions and matrices comprising human recombinant GDF5 that are suitable for treating such deficits.

DETAILED DESCRIPTION OF THE INVENTION

Neurogenesis has been demonstrated in the adult hippocampus, subventricular zone, substantia nigra, and olfactory bulbs. Thus, agents that can recruit and/or differentiate these cells into DA specific neurons are essential for providing cell replacement in treating neurological deficits resulting from injury or disease to the striatum or substanta nigra pars compacta of a human that may be attributable to Parkinson' disease. In methods of treatment and compositions of the present invention, human recombinant GDF5 is utilized as a pre-differentiation or differentiation agent to differentiate stem or progenitor cell populations, whether endogenous or exogenous. The invention is based, at least in part, on the discovery that human recombinant GDF5 is a neurotrophic factor that selectively induces adult neural hippocampal progenitor cells to differentiate towards a dopaminergic phenotype. The data described herein demonstrate that human recombinant GDF5 is a potent inducer of neural stem cell differentiation. These results thus demonstrate the synergistic utility of human recombinant GDF5 for providing neuroregenerative function, in addition to its neuroprotective function.

GDF5 is a protein that functions as a growth and differentiation factor. The protein may be found in its natural state in mammals. Naturally occurring human GDF5 may be modified, purified or otherwise treated to form human recombinant GDF5, as further described herein and as those skilled in the art would understand. "Human recombinant GDF5" will be referred to generically herein as GDF5-HR.

Known GDF5-HR proteins include BMP-14, CDMP-1 and MP52.

MP52, available from Biopharm GmbH, a German corporation having a place of business in Heielberg, Germany, was first isolated for its cDNA as an osteogenetic factor belonging to TGF-beta gene superfamily in 1994. MP52 is a protein having 120 amino acid residues with alanine at the N-terminus, and its amino acid sequence is reported in WO93/16099 and WO95/04819. It is evident from various animal tests that MP52 is involved in osteogenesis similar to other osteogenetic factors.

Since MP52 has been discovered to be a potent inducer of neural stem cell differentiation, it has been determined that it would be useful for the treatment of neurological deficits in the striatum or substanta nigra pars compacta of a human attributable to neurodegenerative diseases, in particular Parkinson's, or damage caused by stokes affecting the middle cerebral artery (MCA) and its branches. While we have found that MP52 alone can stimulate the differentiation of adult neural progenitors isolated from the hippocampus towards a dopaminergic phenotype, it may be combined with agonists to induce enhanced dopaminergic differentiation in neural stem cells, or in other cells that have the capacity to differentiate towards a dopaminergic phenotype. For example, MP52 may be utilized in combination with Sonic Hedgehog (SHH) or Fibroblast Growth Factor 8 (FGF8), providing a significantly enhanced method for inducing neural stem cells and other cells described herein to become dopaminergic in phenotype. SHH is an integral part of the Wnt signaling pathway; the other factors important in this developmental pathway may be important for neuronal formation in combination with GDF5-HR.

GDF5-HR could also be used to differentiate forms of stem cells other than adult neural progenitors, such as hippocampal progenitor cells or hippocampal stem cells, or other cells having the capacity to differentiate towards a dopaminergic phenotype. These other forms of cells include, but are not limited to, mesenchymal stem cells, hematopoietic stem cells, embryonic stem cells (ESCs), progenitors derived from embryonic stem cells, postpartum-derived stem or progenitor cells, cells derived from umbilical cord or placental tissue, muscle derived stem or progenitor cells, pancreatic-derived stem or progenitor cells, limbal-derived stem or progenitor cells, retinal-derived stem or progenitor cells, and liver-derived stem or progenitor cells.

GDF5-HR may be used singly as a neurotrophic factor to induce cell populations to differentiate in the treatment of neurological deficits in the striatum or substanta nigra pars compacta of a human. The term neurotrophic, as used herein, is defined to include the potential to restore, regenerate and differentiate cells. Also, the protein may be incorporated into a neurotrophic composition or used in conjunction with a suitable matrix that acts as a delivery or support system. The neurotrophic composition will comprise an effective amount of GDF5-HR. By effective amount, it is meant that amount effective to induce cell populations comprising the capacity to differentiate towards a dopaminergic phenotype to in fact differentiate towards said dopaminergic phenotype. Neurotrophic compositions of the present invention may comprise about 0.5 to about 1,000 nanograms of MP52, or about 0.5 to about 200 nanograms of MP52.

A neurotrophic composition may be obtained by fixing, mixing, dissolving or suspending the GDF5-HR in a pharmaceutically acceptable carrier or an aqueous solvent. For example, suitable examples of carriers or aqueous solvents include, but are not limited to, clinical grade sterile water, sterile saline, sterile phosphate buffered saline, dextrose in sterile water, sterile liquid media or other physiologically acceptable isotonic liquids. In addition, the neurotrophic composition of the present invention can contain a variety of pharmacologically acceptable additives, such as a stabilizer, a preservative, a thickener, a solubilizer and the like, which can be combined with the carrier or aqueous solvent.

GDF5-HR may also be used in conjunction with a suitable matrix that acts as a delivery or support system. A successful matrix for a GDF5-HR desirably performs several important functions. It desirably binds the GDF5-HR and acts as a slow or sustained release delivery system, and accommodates each step of the cellular response during differentiation. The matrix would prevent diffusion of GDF5-HR from the site of delivery, thus localizing the effect of the GDF5-HR on the delivered cells. In addition, selected matrix materials should be biocompatible in vivo, porous and preferably biodegradable. The term biodegradable as used herein is defined to include materials that are degraded or broken down (chemically or physically) under physiological conditions in the body such that the degradation products are excretable or absorbable by the body. The biodegradation rate can vary according to the desired release rate once implanted in the striatum or substanta nigra pars compacta. The matrix desirably also acts as a temporary scaffold until replaced by newly grown neural tissue. Therefore, in one embodiment, the matrix provides for sustained release of the neurotrophic factor component to a patient in need of the factor and may provide a structure for developing tissue growth in the patient. The matrix can be in particulate form (macroparticles greater than 10 microns in diameter or microparticles less than 10 microns in diameter), or can be in the form of a structurally stable, three-dimensional implant (e.g., a scaffold). The implant can be, for example, a cube, cylinder, tube, block, film, sheet, or an appropriate anatomical form.

Factors affecting the mechanical performance of in vivo biodegradable polymers are well known to the polymer scientist, and include monomer selection, initial process conditions, and the presence of additives. Biodegradation has been accomplished by synthesizing polymers that have unstable linkages in the backbone, or linkages that can be safely oxidized or hydrolyzed in the body. The most common chemical functional groups having this characteristic are ethers, esters, anhydrides, orthoesters and amides. Therefore, in one embodiment of the present invention, GDF5-HR is controllably released from the biodegradable polymer matrix to the site where it is needed by hydrolysis of chemical bonds in the biodegradable polymer. Biodegradable polymer matrices are preferably in the form of a powder, microparticle, microsphere, strip, gel, such as an in situ polymerizable gel, web or sponge.

The biocompatible matrix may be comprised of natural, modified natural or synthetic biodegradable polymers, including homopolymers, copolymers and block polymers, as well as combinations thereof. It is noted that a polymer is generally named based on the monomer from which it is synthesized.

Examples of suitable biodegradable polymers or polymer classes include fibrin, collagen, elastin, gelatin, vitronectin, fibronectin, laminin, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. For both glycolic acid and lactic acid, an intermediate cyclic dimer is typically prepared and purified prior to polymerization. These intermediate dimers are called glycolide and lactide, respectively. Other useful biodegradable polymers or polymer classes include, without limitation, polydioxanones, polycarbonates, polyoxalates, poly(alpha-esters), polyanhydrides, polyacetates, polycaprolactones, poly(orthoesters), polyamino acids, polyamides and mixtures and copolymers thereof. Additional useful biodegradable polymers include, without limitation stereopolymers of L- and D-lactic acid, copolymers of bis(para-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, polyhydroxy-alkanoates and mixtures thereof. Binary and ternary systems also are contemplated.

In general, a suitable biodegradable polymer for use as the matrix is desirably configured so that it has mechanical properties that are suitable for the intended application, remains sufficiently intact until tissue has in-grown and healed, does not invoke an inflammatory or toxic response, is metabolized in the body after fulfilling its purpose, is easily processed into the desired final product to be formed, demonstrates acceptable shelf-life, and is easily sterilized.

In one aspect of the invention, the biocompatible polymer used to form the matrix is in the form of a hydrogel. In general, hydrogels are cross-linked polymeric materials that can absorb more than 20% of their weight in water while maintaining a distinct three-dimensional structure. This definition includes dry cross-linked polymers that will swell in aqueous environments, as well as water-swollen materials. A host of hydrophilic polymers can be cross-linked to produce hydrogels, whether the polymer is of biological origin, semi-synthetic, or wholly synthetic. The hydrogel may be produced from a synthetic polymeric material. Such synthetic polymers can be tailored to a range of properties and predictable lot-to-lot uniformity, and represent a reliable source of material that generally is free from concerns of immunogenicity. The matrices may include hydrogels formed from self assembling peptides, as those discussed in U.S. Pat. Nos. 5,670,483 and 5,955,343, U.S. Patent Application No. 2002/0160471, PCT Application No. WO02/062969.

Properties that make hydrogels valuable in drug delivery applications include the equilibrium swelling degree, sorption kinetics, solute permeability, and their in vivo performance characteristics. Permeability to compounds, including GDF5-HR, depends in part upon the swelling degree or water content and the rate of biodegradation. Since the mechanical strength of a gel declines in direct proportion to the swelling degree, it is also well within the contemplation of the present invention that the hydrogel can be attached to a substrate so that the composite system enhances mechanical strength. In alternative embodiments, the hydrogel can be impregnated within a porous substrate, so as to gain the mechanical strength of the substrate, along with the useful delivery properties of the hydrogel for GDF5-HR In one embodiment, it is possible that a direct intraparenchymal injection into the substantia nigra pars compacta or corpus striatum of GDF5-HR, or a neurotrophic composition comprising GDF5-HR, or a matrix comprising the GDF5-HR, may be effective to promote differentiation of a residual pool of progenitor or stem cells to differentiate localized niches of the neural progenitor or stem cells towards the dopaminergic lineage.

Alternatively, the GDF5-HR neutrophic compositions and/or matrices comprising the GDF5-HR may be delivered to the site via direct implantation, via a micro catheter, intracatheterization, or via a mini-pump. The GDF5-HR compositions and/or matrices could also be indirectly delivered to the substantia nigra pars compacta or corpus striatum via intrathecal delivery, or intracerebroventricularly, or by intranasal administration. The vehicle excipient or carrier can be any of those known to be pharmaceutically acceptable for administration to a patient, particularly locally at the site at which cellular differentiation is to be induced. Examples include liquid media, for example, Dulbeccos Modified Eagles Medium (DMEM), sterile saline, sterile phosphate buffered saline, Leibovitz's medium (L15, Invitrogen, Carlsbad, Calif.), dextrose in sterile water, and any other physiologically acceptable liquid.

A preferred method of delivery into the substantia nigra pars compacta is intrathecally or intracerebroventricularly with, for example, an Ommaya reservoir in accordance with known techniques such as those taught in F. Balis & D. Poplack, Am. J. Pediatric. Hematol. Oncol. 11(1):74-86. (1989). An even more preferred method of delivery into the substantia nigra pars compacta is by direct intraparenchymal injection via a micro catheter.

In an alternate embodiment, GDF5-HR could be used to pre-treat adult stem or progenitor cells prior to implantation, or added in combination with such cells in a device prior to implantation to induce in vivo up-regulation of these transcripts in cell populations in the brain, or alternatively to force the differentiation of neural stem or progenitor pools in the brain. Thus, these conditions could be utilized to pre-treat cell pools prior to implantation in the corpus striatum or substantia nigra, including neural stem or progenitor cells, or other stem or progenitor cell, or other cells described herein. For example, hippocampal neural stem cells can be differentiated on a suitable matrix/scaffold with GDF5-HR and transplanted directly in their differentiated form into the striatum or substantia nigra pars compacta.

The following samples are provided to further describe certain aspects of the present invention and are not intended to limit the scope of the invention.

EXAMPLE 1

MP52-Induced Differentiation of Adult Rodent Hippocampal Neural Progenitors Towards a Dopaminergic Phenotype Adult rodent hippocampal neural progenitors were isolated from adult rat brain following previously published methods [Svendson et al., Nat Rev Genet., 5(2) 136-44 (2004)]. Isolated cells were seeded at 1,000 cells/cm$^2$ into laminin-coated 24 well tissue culture plates (Becton Dickson, Bedford, Mass.).

Seeded cells were initially grown in a supplemented neuralbasal medium (NBM). The NBM was Neurobasal-A media (Invitrogen, Carlsbad, Calif.) with B27 supplement (Invitrogen, Carlsbad, Calif.), and L-glutamine (4 milliMolar) (Sigma, St. Louis, Mo.). Supplemented NBM also contains epidermal growth factor (EGF) (Sigma, St. Louis, Mo.), at 20 nanograms/milliliter, and basic fibroblast growth factor, (bFGF) (Peprotech, Rocky Hill, N.J.), at 20 nanograms/milliliter).

Set one of cells was cultured in supplemented NBM for 17 days. Set two of cells was initially cultured in supplemented NBM for 4 days. The supplemented NBM then was removed from the culture plates and cells were cultured in NBM containing MP52 (Biopharm GmbH, Heidelberg, Germany) at 20 nanograms/milliliter for a period of 13 days. Set three of cells was initially cultured in supplemented NBM for 10 days. The supplemented NBM then was removed from the culture plate, and cells were cultured in NMB containing Sonic Hedgehog, (SHH) (Sigma, St. Louis, Mo.), at 200 nanograms/milliliter, and fibroblast growth factor 8 (FGF8) (Peprotech, Rocky Hill, N.J.), at 100 nanograms/milliliter. Set four of cells was initially cultured in supplemented NBM for 10 days. The supplemented NBM then was removed from the culture plates and cells were cultured in NBM containing MP52 at 20 nanograms/milliliter, SHH at 200 nanograms/milliliter, and FGF8 at 100 nanograms/milliliter).

At the end of the 17-day experimental period, all cultures were fixed with 4 percent paraformaldehyde (Sigma, St. Louis, Mo.) and immunocytochemical staining was performed to evaluate expression of Beta Tubulin III (TuJ1), glial fibrilary acidic protein (GFAP), and tyrosine hydroxylase (TH).

Briefly, fixed cultures were washed with phosphate-buffered saline (PBS) (Invitrogen, Carlsbad, Calif.) and exposed to a protein-blocking solution for 30 minutes. The protein-blocking solution was PBS with 4% goat serum (Chemicon, Temecula, Calif.), and 0.3% Triton (Triton X-100, Sigma). Primary antibody solutions were then applied to the samples containing the blocking solution plus TuJ1 antibody (Sigma, St. Louis, Mo.) at 1:500 dilution, GFAP antibody (Chemicon, Temecula, Calif.) at 1:1,000 dilution, and TH (Chemicon, Temecula, Calif.) at 1:2,000 dilution for a period of 1 hour at room temperature.

The primary antibody solutions were removed and samples were washed with PBS. A secondary antibody solution then was applied for 1 hour at room temperature. The secondary antibody solution was protein-blocking solution with goat anti-mouse IgG—Texas Red (Chemicon, Temecula, Calif.) at 1:250 dilution, and goat anti-rabbit IgG—Alexa 488 (Chemicon, Temecula, Calif.) at 1:250 dilution. Samples were then washed and incubated with 10 micromolar 4'-6-Diamidino-2-phenylindole-2HCl (DAPI) (Molecular Probes, Eugene, Oreg.) for 10 minutes to visualize cell nuclei.

Following immunocytochemical staining, fluorescence was visualized using an Olympus inverted epifluorescent microscope and images were taken with a digital camera and ImagePro software (Media Cybernetics, Silver Spring, Md.). To further quantify the response, fields of cells were counted at a magnification power of 200× to examine the percentage of positive cells for each marker and compared to control samples grown in NBM alone. A minimum of 1,000 cells were counted per condition or, if less, the total number of cells observed in that condition.

The percentage of cells positive for a given marker was determined by dividing the number of positive cells for a particular marker by the total number of nucleated cells determined by DAPI staining. Table 1 shows the percentage of cells that stained positive for TuJ1, TH, and GFAP.

TABLE 1

Percentage of cells staining positive for a given marker.

| CELL CONDITIONS | IMMUNOSTAIN | | |
| --- | --- | --- | --- |
|  | TuJ1 | TH | GFAP |
| Supplemented NBM | 20.1% | 8.8% | 5.5% |
| NBM + MP52 | 12.5% | 6.1% | ≥80% |
| NBM + SHH + FGF8 | 35.9% | 9.0% | 59.5% |
| NBM + SHH + FGF8 + MP52 | 32.4% | 26.0% | ≥60% |

The table shows that with NBM plus FGF8 and SHH alone, 9 percent of these neural progenitor cells differentiated into a dopaminergic phenotype (as demonstrated by TH positive staining). Dopaminergic differentiation was significantly enhanced when MP52 was combined with FGF8 and SHH (26 percent TH positive). Furthermore, MP52 also induced the differentiation of these neural precursor cells towards an astrocytic phenotype, as evidenced by increased expression of the intermediate filament protein GFAP, as demonstrated with immunocytochemistry. While the total number of neurons (TuJ1 positive cells) did not significantly change whether MP52 was added in combination with SHH and FGF8, the percentage of these cells that matured towards a dopaminergic TH positive phenotype did increase significantly in the presence of MP52.

EXAMPLE 2

MP52-Induced Nurr1 Expression in Postpartum Cells

Postpartum cells were isolated from an umbilical cord and placental digestion as described in U.S. patent application Ser. Nos. 10/887,012 and 10/877,446. Briefly, human umbilical cord and placental cells were isolated from explants of postpartum tissue.

The tissues were obtained from a pregnancy at the time of parturition or a normal surgical delivery. The following cell isolation protocols were performed under aseptic conditions in a laminar flow hood.

The postpartum tissues were washed in phosphate buffered saline (PBS) in the presence of antimycotic and antibiotic (AA) (1 milliliter per 100 milliliter (10,000 Units per milliliter)) (PBS-AA). The washing step consisted of rinsing the tissue with PBS-AA using gentle agitation. This process was performed several times to remove blood and debris. The washed tissues were then mechanically dissociated in 150 cm tissue culture plates in the presence of 50 milliliter of DMEM-Low glucose (DMEM:Lg) or DMEM-high glucose (DMEM:Hg) medium.

Once the tissues were chopped into small pieces, they were transferred to 50-milliliter conical tubes with approximately 5 gm of tissue per tube. The tissue was then digested in 40 milliliters DMEM:Lg or DMEM:Hg containing AA with 10 milliliters of collagenase:dispase (C:D) dissolved in DMEM or collagenase:dispase:hyaluronidase (C:D:H) dissolved in DMEM. C:D was 750 milligram of collagenase type II (>125 Units per milligram (0.5-3 FALGA Units per milligram)) with 500 milligram dispase (0.4 Units per milligram) diluted in 50 milliliters of DMEM. Thus, C:D:H was 750 milligram of collagenase type II (>125 Units per milligram (0.5-3 FALGA Units per milligram)) with 500 milligram dispase (0.4 Units per milligram) with 200 milligram (300 Units per mg) diluted in 50 milliliter of DMEM. Alternatively, collagenase type IV (750 milligram at >125 Units per milligram (0.5-3 FALGA Units per milligram)) was also utilized in this protocol. The conical tubes containing the tissue, medium and digestion enzymes were incubated in an orbital shaker (medium shaking) at 37° C. for less than 24 hours.

After digestion the tissues were filtered with 40-micrometer nylon cell strainers. The filtered cell suspensions were then centrifuged at 1000×g for 10 minutes. The supernatant was aspirated and the cell pellet resuspended in 50 milliliters of fresh medium. This process was completed twice to remove residual enzyme activity from the cell populations. Supernatant was then removed and the cell pellets were resuspended in 2 milliliters of expansion medium (DMEM:Lg or DMEM:Hg; 15 percent FBS (Hyclone Defined bovine serum Lot#AND18475); 2-mercaptoethanol (1 microliter per 100 milliliters); antibiotic per antimycotic (1 milliliter per 100 milliliters (10,000 Units per milliliter)). Cell viability per numbers of cells isolated was determined by a manual count of trypan blue exclusion.

Isolated umbilical and placental cells were seeded at 1,000 cells/cm$^2$ into laminin coated 24 well tissue culture plates (Corning, N.Y.). Cells were initially seeded in maintenance media (control) as described in nonprov serial no. After 4 days in maintenance media, cells were split into four groups. The first set of cells was switched to NBM supplemented with EGF (20 nanograms/milliliter) and bFGF (20 nanograms/milliliter) and grown for 13 days. Sets two through four were switched to NBM supplemented with EGF (20 nanograms/milliliter) and bFGF (20 nanograms/milliliter) and grown for 6 days. The NBM supplemented with EGF and FGF8 was then removed and cells were cultured in NBM containing; MP52 plus SHH plus FGF8 (set two); MP52 plus SHH plus FGF8 plus retinoic acid (RA) (set three); or MP52 plus RA (set four) for a further 7 days of culture.

At the end of the 17-day experimental period, RNA was isolated from the induced cell population using an Rneasy kit (RNeasy Mini kit, Qiagen, Valencia, Calif.). Cells were lysed with 350 microliters buffer RLT containing beta-mercaptoethanol (Sigma St. Louis, Mo.) according to the manufacturer's instructions (RNeasy Mini kit, Qiagen, Valencia, Calif.) and stored at −80° C. Cell lysates were thawed and RNA extracted according to the manufacturer's instructions, with a 2.7 U/sample DNase treatment (Sigma St. Louis, Mo.). RNA was eluted with 50 microliters of DEPC-treated water (0.1 percent diethylpyrocarbonate, Sigma, St. Louis, Mo.) and stored at −80° C. RNA was reverse transcribed using random hexamers with the TaqMan reverse transcription reagents (Applied Biosystems, Foster City, Calif.) at 25° C. for 10 minutes, 37° C. for 60 minutes and 95° C. for 10 minutes. Samples were stored at −20° C.

Qauntitative PCR (Q-PCR) was performed on cDNA samples using Assays-on-Demand™ gene expression products Nurr I (Hs00428691), Tyrosine Hydroxylase (Hs00428691), and GAPDH (Applied Biosystems, Foster City, Calif.) and TaqMan Universal PCR master mix according to the manufacturer's instructions using a 7000 sequence detection system with ABI prism 7000 SDS software. Thermal cycle conditions were initially 50° C. for 2 min and 95° C. for 10 min, followed by 40 cycles of 95° C. for 15 sec and 60° C. for 1 min.

Nurr1 and tyrosine hydroxylase (TH) mRNA expression following differentiation of postpartum cells is shown in Table 2. The table shows that MP52 induced Nurr1 and TH expression in postpartum cells. Nurr1 expression was induced in postpartum cell cultures following incubation with SHH plus FGF8 plus MP52, or SHH plus FGF8 plus MP52 plus retinoic acid, when compared to control (NBM plus EGF plus FGF8). Nurr1 induction was further increased compared to control when postpartum cells were incubated with MP52 in combination with retinoic acid only. Tyrosine hydroxylase (TH) expression was induced in umbilical cell cultures following incubation with SHH plus FGF8 plus MP52, SHH plus FGF8 plus MP52 plus retinoic acid, or MP52 plus retinoic acid, compared to control (neurobasal medium plus B27 supplement plus EGF/FGF).

TABLE 2

Nurr1 and tyrosine hydroxylase expression in postpartum cells following dopaminergic differentiation

| Cell Type/Gene | Control | SHH/FGF8/MP52 | SHH/FGF8/ RA/MP52 | RA/MP52 |
|---|---|---|---|---|
| Umbilicus (Nurr1) | 1 | 3.9 | 4.5 | 8.34 |
| Placenta (Nurr1) | 1 | 3.85 | 1.39 | 14.32 |
| Umbilicus (TH) | 1 | 0 | 2.73 | 0 |
| Placenta (TH) | 1 | 0 | 0 | 0 |

Key:
SHH = Sonic Hedgehog;
FGF8 = Fibroblast Growth Factor 8;
RA = Retinoic Acid

EXAMPLE 3

MP52-Induced Differentiation of Adult Rodent Hippocampal Neural Progenitors Toward Oligodendrocytes and Astrocytes Microspherical cores containing MP52 were prepared by a double-emulsion technique. In brief, 50 mg of a 90:10 copolymer of poly(D,L-lactic-co-glycolic) acid (sold under the tradename MEDISORB, Alkermes, Inc., Wilmington, Ohio), with an intrinsic viscosity of 0.4 dl/gm, was dissolved in 1.5 ml of methylene chloride and 0.5 ml of acetone. 25 micrograms of MP52 was dissolved in 0.15 ml of 16 mM citrate buffer (pH 6.0) containing 0.1 percent (wt./vol.) human serum albumin (HSA) (Sigma, St, Louis, Mo.). MP52 was reconstituted with excipients to stabilize the protein prior to incorporating it into the microspheres. The polymer/MP52 aqueous solution was sonicated continuously using a Branson Sonifier 450 (Branson Ultrasonics, Danbury, Conn.) by pulsing for 10 seconds to yield a single emulsion. The single emulsion was added into 30 ml of an aqueous solution containing 5 percent (wt./vol.) polyvinyl alcohol (MW 31,000-50,000, 87-89 percent hydrolyzed; Aldrich Chemical Company, Milwaukee, Wis.) and 5 percent (wt./wt.) NaCl. The resulting solution was magnetically stirred for 1 minute, which generated a double emulsion.

The double emulsion (water/oil/water) was added to deionized water (400 milliliters) containing 10 percent (wt./wt.) NaCl and magnetically stirred for 25 minutes. The microspherical cores were then filtered through a 40-micron nylon cell strainer (Becton Dickinson, N.J.) and washed with deionized water (400 ml). The cores were then frozen for 2 hours at −80° C. Microspheres were then freeze-dried by a lyophilization process using a Virtis Freezemobile (Virtis Company, Gardinier, NYC). Microspheres were lyophilized retaining an ambient temperature of −40° C., and stored in sterile microvials at 4° C. until further use.

Freeze-dried microspheres were washed several times in neurobasal-A culture medium to remove debris. Washed microspheres were coated with laminin (Sigma, St. Louis, Mo.) at 20 microgram/milliliter. 20 to 50 laminin coated microspheres were mixed with 500,000 adult rodent neural progenitor cells, prepared following the method described in Example 1, in a sterile eppendorf (Ambion, Austin, Tex.) in 1 milliliter of neurobasal-A medium for 10 to 30 minutes. This core/cell suspension was seeded into 2 wells (500 microlitres/well) of a 24 well ultra low cluster tissue culture plate (Corning Inc., Corning, N.Y.). 100 microlitres of fresh medium was supplemented into each well for an additional 5 days.

At the end of the experimental period, cells attached to the microspheres were fixed with 4 percent paraformaldehyde and immunocytochemistry was performed to evaluate expression of GFAP (GFAP, 1:1000, DakoCytomation, Carpinteria, Calif.) and myelin basic protein (MBP, 1:500, Chemicon, Temecula, Calif.). For appropriate preparation of samples for staining, fixed, cell-coated microspheres were centrifuged at 100 times g for 3 minutes in a 15 ml conical test tube. The pellet was then resuspended in a small volume of sterile PBS. The mixture was plated with a micropipette into the center of a weigh boat dish. OCT embedding compound (Tissue-Tek OCT Compound, Sakura, Torrance, Calif.) was added around the small pellet until filling the weigh boat. The weigh boat was then placed on top of a freezing bath of ethanol and dry-ice to rapidly reduce the temperature of the OCT, thereby embedding the cell-coated microspheres in a hard block.

10-micron sections were then cut using a standard cryostat (Leica) and placed onto a glass slide for staining. A hydrophobic pen was used to create a hydrophobic surface around the sections for staining. Immunostaining was performed just as before in Example 1, this time with antibodies directed against GFAP and MBP (1:500, myelin basic protein, Chemicon, Temecula, Calif.) at the aforementioned concentrations.

Immunohistochemistry demonstrated the differentiation of adult rodent hippocampal neural progenitors seeded on MP52-loaded microspheres. MP52-loaded microspheres induced the differentiation of a significant number of adult rodent neural progenitor cells into GFAP positive astrocytes and myelin basic protein positive oligodendrocytes. This effect was not observed in control particles not loaded with MP52.

Herein, we provide evidence for the utilization of MP52 as an agent to treat Parkinsonian deficits in humans by using it to differentiate either endogenous or exogenous (transplanted) stem, or progenitor-like cells or other applicable cells into a dopaminergic phenotype. This approach can be used to ameliorate such deficits in the adult resulting from the loss of dopaminergic neurons projecting from the substantia nigra pars compacta to the corpus striatum. The robust differentiation capacity of MP52 in this application particularly related to hippocampal neural progenitors provides a therapeutic means for generating large numbers of dopaminergic cells for Parkinson's treatment.

We claim:

1. A method for differentiating cells isolated from mammalian umbilical cord tissue substantially free of blood towards a dopaminergic phenotype, comprising treating the cells isolated from mammalian umbilical cord tissue substantially free of blood with a composition comprising human recombinant GDF5, Sonic Hedgehog, retinoic acid and FGF8 in an amount sufficient to induce the cells isolated from mammalian umbilical cord tissue substantially free of blood to differentiate towards a dopaminergic phenotype.

2. The method of claim 1, wherein the human recombinant GDF5 is selected from the group consisting of MP52, BMP-14 and CDMP-1.

3. The method of claim 1, wherein the human recombinant GDF5 is MP52.

* * * * *